(12) United States Patent
Lin (10) Patent No.: US 10,995,411 B2
(45) Date of Patent: May 4, 2021

(54) GAS GENERATOR (71) Applicant: Hsin-Yung Lin, Shanghai (CN)

(72) Inventor: Hsin-Yung Lin, Shanghai (CN)

( * ) Notice: Subject to any disclaimer, the term of this patent is extended or adjusted under 35 U.S.C. 154(b) by 245 days.

(21) Appl. No.: 15/971,319

(22) Filed: May 4, 2018

(65) Prior Publication Data

US 2018/0320274 A1    Nov. 8, 2018

(30) Foreign Application Priority Data

May 4, 2017 (CN) .......................... 201710306958.7

(51) Int. Cl.
| C25B 1/04 | (2021.01) |
| C02F 1/461 | (2006.01) |
| A61M 16/10 | (2006.01) |
| A61M 16/16 | (2006.01) |
| C25B 15/08 | (2006.01) |
| C25B 11/00 | (2021.01) |

(52) U.S. Cl.
CPC .............. *C25B 1/04* (2013.01); *A61M 16/101* (2014.02); *A61M 16/161* (2014.02); *C02F 1/4618* (2013.01); *C25B 11/00* (2013.01); *C25B 15/08* (2013.01); *A61M 16/107* (2014.02); *A61M 2202/0208* (2013.01); *C02F 1/46109* (2013.01)

(58) Field of Classification Search
CPC ......... Y02E 60/36; Y02E 60/32; C25B 15/08; C25B 1/04; C25B 9/00; C25B 15/00; C25B 9/06; C25B 15/02; C25B 1/00; C25B 1/02; C25B 1/06; C25B 9/18
See application file for complete search history.

(56) References Cited

U.S. PATENT DOCUMENTS

| 2005/0056661 A1* | 3/2005 | Casamatta ........ H01M 8/04089 222/3 |
| 2011/0072887 A1* | 3/2011 | Oki ......................... B03C 3/014 73/28.02 |
| 2016/0108528 A1* | 4/2016 | Lin ...................... A61M 16/107 204/276 |

FOREIGN PATENT DOCUMENTS

| CN | 103361667 A | 10/2013 |
| CN | 105617503 A | 6/2016 |
| CN | 206089830 U | 4/2017 |

* cited by examiner

*Primary Examiner* — Zulmariam Mendez (57) ABSTRACT

The present invention provides a gas generator and comprises an electrolytic device, a condensing filter device, and a cooling device. The electrolytic device is configured for electrolyzing electrolyzed water to generate hydrogen. The condensing filter device is coupled to the electrolytic device for receiving and filtering the hydrogen generated by the electrolytic device. The cooling device comprises a cooling sheet and a cooling fan, wherein the cooling sheet is configured on the condensing filter device, and the cooling fan is configured for driving air to flow through the cooling sheet to cool the condensing filter device. The present invention uses the condensing filter device and the cooling device for cooling the generated gas and the component that gas passes through, so that a stable operating temperature is maintaining. Therefore, the possibility of the component damage by high temperature and humidity is reduced.

20 Claims, 5 Drawing Sheets

GAS GENERATOR

CROSS-REFERENCE TO RELATED APPLICATIONS

This application claims the priority benefit of Chinese Application Serial No. 201710306958.7 filed May 4, 2017 the disclosure of which is incorporated herein by reference.

FIELD OF THE INVENTION

The present invention relates to a gas generator, more particularly, to a gas generator having a cooling component to cool down the gas and the interior components.

DESCRIPTION OF THE PRIOR

As people have always been paying much attention on health developments, many developments in medical technology are often targeted on treating diseases and prolonging human life. Most of the treatments in the past are passive, which means that the disease is treated only when it occurs. The treatments include an operation, a medication treatment, a radiation therapy, or even a medical treatment for cancer. However, in recent years, most of the researches from medical experts are gradually moving towards preventive medical methods, such as research on healthy food, screening and the prevention of inherited diseases, which actively prevents diseases from occurring in the future. Due to the focus of the prolongation of human life, many anti-aging and anti-oxidation technologies including skin care products and anti-oxidation food/medicine are gradually being developed and have becoming increasingly popular to the general public.

Studies have found that there are instable oxygen species (O+), also known as free radicals, in the human body. The free radicals which are usually generated due to diseases, diet, environment and one's lifestyle can be excreted in the form of water by reacting with the inhaled hydrogen. With this method, the amount of free radicals in the human body can be reduced, thereby restoring the body condition from an acidic state to an alkaline state, achieving an anti-oxidation, anti-aging and beauty health effect, and even eliminating chronic diseases. Furthermore, there are also clinical experiments showing that patients who need to inhale a high concentration of oxygen for an extended period of time would experience lung damage, but the lung damage could be ameliorated by inhaling hydrogen.

However, the general electrolytic device generates hydrogen by using electrolyzed water for inhaling. Since the generated hydrogen is high-temperature, high-humidity, and rich in electrolyte and impurities, elements and pathways are susceptible to corrosion and abrasion. Therefore, the use period of the machine is decreasing rapidly and results in inconvenience and waste.

SUMMARY OF THE INVENTION

Therefore, the present invention provides a gas generator for electrolyzing the electrolyzed water to generate hydrogen. Due to the condensation filtering device and the cooling device are able to cool down the generated hydrogen and the device, the gas generator elements are avoid from the damage by the high temperature and the high humidity gas damage. Therefore, the purpose of improving operational safety and extending the life of the gas generator is achieved.

An object of the present invention is to provide a gas generator comprising an electrolytic device, a condensing filter device, and a cooling device. The electrolytic device accommodates electrolyzed water and the electrolytic device is configured for electrolyzing the electrolyzed water to generate hydrogen. The condensing filter device further comprises a gas pathway, a filter material, and a spacer. Wherein, the gas pathway is configured for receiving the hydrogen, and the filter material is configured within the gas pathway to filter the hydrogen, and the spacer is configured within the condensing filter device for limiting the movement of the filter material within the gas pathway. The cooling device comprises a cooling sheet and a cooling fan, wherein the cooling sheet is coupled to the condensing filter device and the cooling fan drives the external air to flow through the cooling device.

According to another embodiment, the gas generator further comprises an atomizing device coupled to the condensing filter device. The atomizing device is configured for receiving the filtered hydrogen, and the atomizing device generates atomized gas to be mixed with the filtered hydrogen. The cooling device has an accommodating space for accommodating part of the atomizing device.

According to another embodiment, the cooling device has a cooling pathway formed in the cooling device, and the external air flows through the cooling pathway.

According to another embodiment, the cooling device comprises a cooling pathway component coupled to the cooling sheet. The cooling pathway is formed between the cooling pathway component and the cooling sheet.

According to another embodiment, the cooling fan is a blast fan accommodated in the cooling pathway.

According to another embodiment, the gas generator further comprises a gas filter device coupled to the condensing filter device. The gas filter device is configured for further filtering the hydrogen.

According to another embodiment, the gas generator further comprises a check valve coupled to the gas filter device.

According to another embodiment, the gas filter device has an outer wall and an inner wall. The inner wall is filled with an activated carbon, and the outer wall is located outside the inner wall. The hydrogen received by the gas filter device flows into the inner wall via the interspace between the outer wall and the inner wall and is exhausted outside the gas filter device.

According to another embodiment, the gas filter device comprises a removable cover. The activated carbon is accommodated in a space formed by the inner wall and the cover. The gas filter device and the check valve can be withdrawn from the gas generator simultaneously.

According to another embodiment, the filter material is composed of a plurality of filter pieces. The spacer prevents the filter pieces from connecting to each other directly.

Another aspect of the present invention is to provide a gas generator comprising an electrolytic device, a condensing filter device, and a cooling device. The electrolytic device accommodates electrolyzed water and is configured for electrolyzing the electrolyzed water to generate hydrogen. The condensing filter device is coupled to the electrolytic device for receiving and filtering the hydrogen. The cooling device has a cooling pathway and a plurality of openings, wherein the openings are located on the cooling pathway respectively. The cooling device further comprises a cooling sheet, a cooling pathway component, and a cooling fan. The cooling sheet is coupled to the condensing filter device, and the cooling pathway component is coupled to the cooling sheet, and the cooling pathway is formed between the cooling pathway component and the cooling sheet, and the cooling fan drives the external air to flow through the cooling pathway via the openings.

According to another embodiment of the present invention, the gas generator further comprises an atomizing device coupled to the condensing filter device. The atomizing device is configured for receiving the filtered hydrogen, and the atomizing device generates atomized gas to be mixed with the filtered hydrogen. The cooling device has an accommodating space to accommodate part of the atomizing device.

According to another embodiment, the cooling fan is a blast fan accommodated in the cooling pathway.

According to another embodiment, the gas generator further comprises a gas filter device coupled to the condensing filter device. The gas filter device is configured for further filtering the hydrogen.

According to another embodiment, the gas generator further comprises a check valve coupled to the gas filter device.

According to another embodiment, the check valve is a fire-proof device.

According to another embodiment, the check valve receives the hydrogen exhausted from the gas filter device.

According to another embodiment, the gas filter device has an outer wall and an inner wall. The inner wall is filled with an activated carbon, and the outer wall is located outside the inner wall. The hydrogen received by the gas filter device flows into the inner wall via the interspace between the outer wall and the inner wall and is exhausted outside the gas filter device.

According to another embodiment, the gas filter device comprises a removable cover. The activated carbon is accommodated within a space formed by the inner wall and the cover. The gas filter device and the check valve can be withdrawn from the gas generator simultaneously.

According to another embodiment, the gas filter device has a top and a bottom, and the hydrogen received by the gas filter device flows into the interspace between the outer wall and the inner wall via the top, and then the hydrogen flows into the inner wall from the bottom and is exhausted outside the gas filter device via the top.

In summary, the object of the present invention is to provide a gas generator comprising the electrolytic device, the condensing filter device, and the cooling device. In the gas generator of the present invention, the electrolytic device generates hydrogen for inhaling. The generated gas and the components are cooled down and filtered by the cooling device and the condensing filter device. Therefore, the gas generator works at stable operating temperature, and the gas generator elements are prevented from the damage by the high temperature and the high humidity gas damage. Therefore, the operational safety is improving and the life of the gas generator is extending.

BRIEF DESCRIPTION OF THE APPENDED DRAWINGS

Some of the embodiments will be described in detail, with reference to the following figures, wherein like designations denote like members, wherein.

The advantages, spirits, and features of the present invention will be explained and discussed with embodiments and figures as follows

DETAILED DESCRIPTION OF THE INVENTION

A detailed description of the hereinafter described embodiments of the disclosed apparatus and method are presented herein by way of exemplification and not limitation with reference to the Figures. Although certain embodiments are shown and described in detail, it should be understood that various changes and modifications can be made without departing from the scope of the appended claims. The scope of the present invention will in no way be limited to the number of constituting components, the materials thereof, the shapes thereof, the relative arrangement thereof, etc., and are disclosed simply as an example of embodiments of the present invention.

In the description of the present specification, the terminologies "in an embodiment", "in another embodiment", or "in some embodiments" means that the specific feature, structure, material or characteristic of the present embodiment is involved in at least one embodiment of the present invention. In the description of the present specification, the schematic representation of the mentioned terminologies does not necessarily refer to the same embodiment. Furthermore, the described specific feature, structure, material or characteristic can be involved in any one or more embodiments in a proper way.

In the embodiments of the present specification, the terminology "or" includes the combination of part of listed components, and the combination of all the listed components. For example, the described "A or B" includes only A, only B, and both A and B. Moreover, the terminologies "a" and "the" before the element or component of the present invention do not limit the number of element or component. Therefore, the terminologies "a" and "the" should be read as including one or at least one. Besides, the singular form of element or component also includes the plural form, unless the number clearly refers to the singular form.

Figure 1:
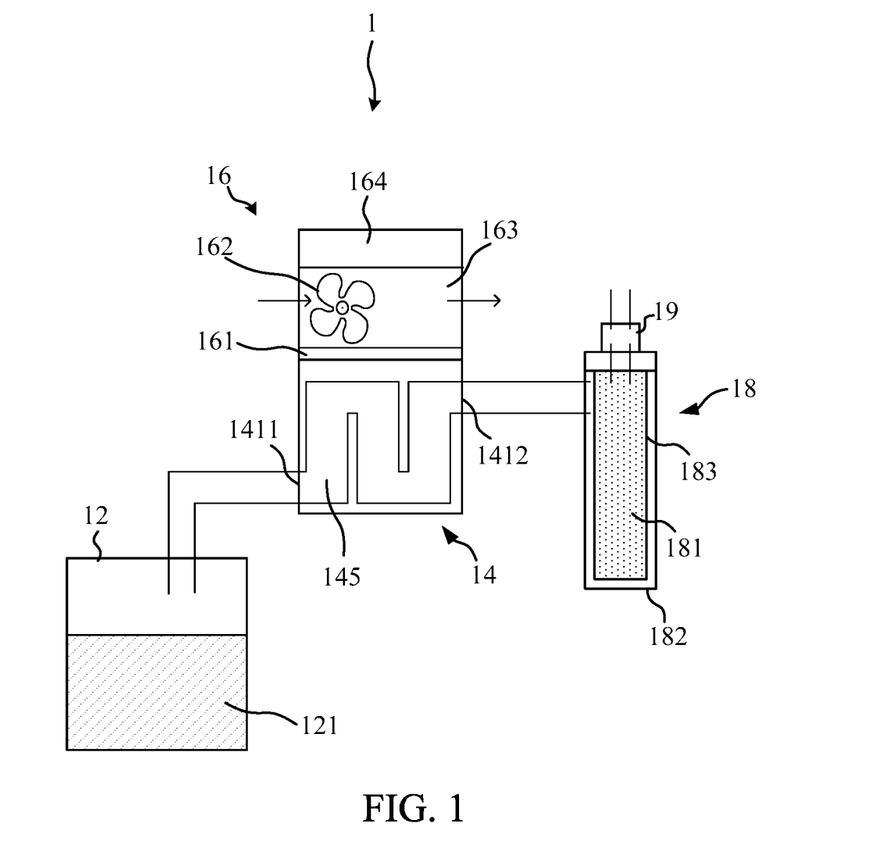
FIG. 1 shows a schematic diagram of an embodiment of the gas generator of the present invention.
Figure 2:
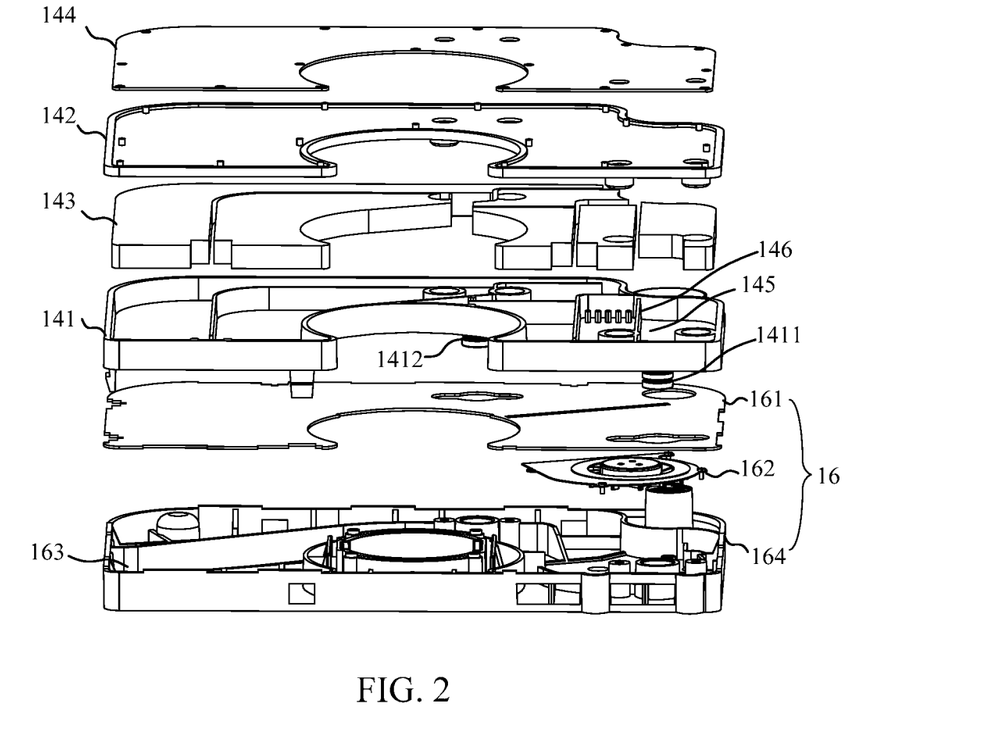
FIG. 2 shows an explosion diagram of an embodiment of the condensing filter device of the gas generator of the present invention.

Please refer to FIG. 1 and FIG. 2. FIG. 1 shows a schematic diagram of an embodiment of the gas generator 1 of the present invention. FIG. 2 shows an explosion diagram of an embodiment of the condensing filter 14 device of the gas generator 1 of the present invention. According to another embodiment, the present invention provides a gas generator 1 comprising an electrolytic device 12, a condensing filter device 14, and a cooling device 16. The electrolytic device 12 accommodates electrolyzed water 121 and the electrolytic device 12 is configured for electrolyzing the electrolyzed water 121 to generate hydrogen. The condensing filter device 14 further comprises a gas pathway 145, a filter material 143, and a spacer 146. Wherein, the gas pathway 145 is configured for receiving the hydrogen, and the filter material 143 is configured within the gas pathway 145 to filter the hydrogen, and the spacer 146 is configured in the condensing filter device 14 to limit the movement of the filter material 143 in the gas pathway 145. The cooling device 16 comprises a cooling sheet 161 coupled to the condensing filter device 14 for conducting heat of the condensing filter device 14. The cooling device 16 further comprises a cooling fan 162 for driving the external air to flow through the cooling device 16. Furthermore, the cooling fan 162 is configured for blowing toward the cooling sheet 161 to take heat away from the cooling sheet 161, so that the temperature of the cooling sheet 161 and the condensing filter device 14 is reduced. It should be noted that the "limit" of the present invention does not mean "fix", but the movement of the filter material 143 is reduced.

In practice, the electrolytic device 12 may be a two-electrode type electrolytic cell. When the electrolytic cell is energized, both electrodes of the cell can simultaneously electrolyze the water to produce hydrogen and oxygen. If the generated gas is accommodated in the same space, the mixed gas of hydrogen and oxygen can be generated. The ratio of hydrogen to oxygen in the mixed gas of hydrogen and oxygen is about 2:1.

In another practice, the electrolytic device 12 may be an ion membrane electrolytic device. The ion exchange membrane is set between an anode chamber and a cathode chamber, wherein oxygen is generated by an anode electrode in the anode chamber and hydrogen is generated by a cathode electrode in the cathode chamber. Besides, the ion membrane electrolytic device can further comprise a gas flow meter connected to the anode chamber and the cathode chamber respectively, so that the concentration ratio of hydrogen and oxygen is regulated as-needed and the mixed gas of hydrogen and oxygen is outputted. In an embodiment, the mixed gas of hydrogen and oxygen may be pure hydrogen, pure oxygen, or any proportion of the hydrogen and oxygen for inhaling. Furthermore, external gas can be accessed. The generated hydrogen, oxygen or the mixed gas of hydrogen and oxygen may be mixed with the external gas to a concentration ratio as-needed for different subsequent applications. Wherein, the external gas may be air, water vapor, volatile gas or noble gas.

Since the gas generated by the electrolytic device 12 may be high temperature or produce water vapor due to the operating environment and generating method, the generated gas is at high temperature and humidity. Furthermore, the vapor may contain not only the electrolyzed water, but also the electrolytes or impurities in the electrolyzed solution. Therefore, the generated gas contains pure hydrogen, pure oxygen, or the mixed gas of hydrogen and oxygen as-needed, and also contains unnecessary moisture, electrolytes, or impurities. The gas with high temperature, high humidity, and impurities is not suitable for human inhalation, meanwhile, the gas pathway and the elements which gas passes through in the gas generator 1 may be damaged. At last, the use period of the machine is decreasing. Therefore, the hydrogen generated by the electrolytic device 12 has to be condensed and filtered.

Please refer to FIG. 2 again. The gas pathway 145 may be formed by combining a condensing lower cover 141 and a condensing upper cover 142. The spacer 146 may be formed on the condensing lower cover 141 or be formed on the condensing upper cover 142. In practice, the spacer 146 may be removably configured on the condensing lower cover 141 or the condensing upper cover 142; or the spacer 146 may be formed with the condensing lower cover 141 or the condensing upper cover 142 in an integrally formed manner. Wherein, the condensing lower cover 141 has a condensing inlet 1411 coupled to the electrolytic device 12 to receive the hydrogen generated by the electrolytic device 12. The condensing upper cover 142 has a condensing outlet 1412 to output the cooled and filtered hydrogen. The hydrogen received by the condensing filter device 14 flows through the filter material 143 to filter out the electrolytes or impurities in the gas. At the same time, the gas can be cooled down so that the vapor in the gas is condensed and leaved in the condensing filter device 14. Wherein, the filter material 143 can be asbestos and may consist of a plurality of filter pieces. Since the filter pieces is configured for filtering and cooling the gas passing through, the filter pieces will contain the impurities, electrolytes, electrolyzed solution or the vapor. The spacer 146 is configured for separating the adjacent filter pieces to block the dialysis between the filter pieces. Therefore, the filter pieces can be kept in well condensation and filtration efficiency. Wherein, the spacer 146 may be a column or a block. Besides, since the condensing filter device 14 is configured for receiving the gas with high temperature, the temperature of the condensing filter device 14 will be increasing. Therefore, a condensing cover cooling fin can be configured to assist in the overall cooling process of the condensing filter device 14 to retain the operation temperature of the condensing filter device 14.

Figure 3:
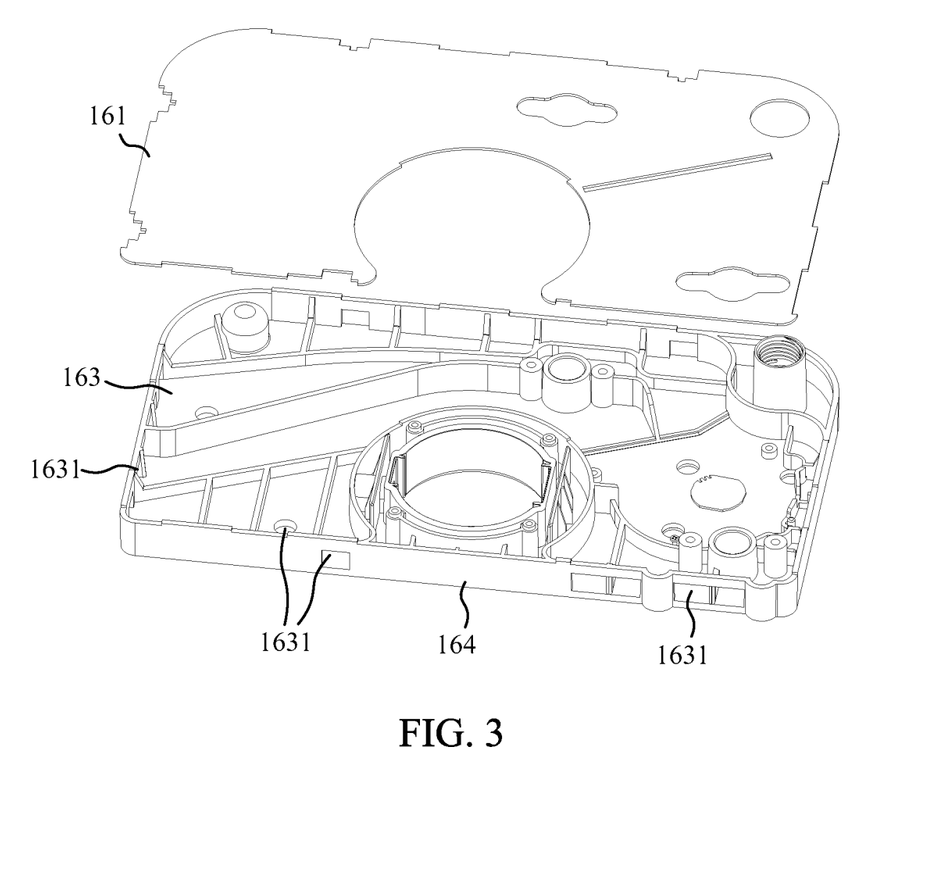
FIG. 3 shows a schematic diagram of the cooling pathway of FIG. 2.

Please refer to FIG. 2 and FIG. 3. FIG. 3 shows a schematic diagram of the cooling pathway 163 of FIG. 2. In practice, the gas generator 1 further comprises a cooling device 16 to cool down the condensing filter device 14. In an embodiment, a cooling sheet 161 of the cooling device 16 may be configured penetrably in the condensing filter device 14 to receive the heat of the condensing filter device 14. In another embodiment, the cooling sheet 161 is removably attached on the surface of the condensing filter device 14 properly. The heat of the condensing filter device 14 is transferred to the cooling sheet 161 due to the heat conduction. In practice, the cooling sheet 161 also can be configured on the surface of the condensing filter device 14. In another embodiment, part of the condensing filter device 14 is made of the cooling sheet 161 to save the material using. Since the cooling sheet 161 has to rapidly absorb the heat of the condensing filter device 14 and transfer the heat to the external, a material with well heat conductivity can be chosen for rapid heat exchange. The cooling sheet 161 can be made of metal, furthermore, the cooling sheet 161 can be made of stainless steel, so that the rustiness caused by the environment humidity, the vapor by electrolyzation, or the accidentally splashed electrolyzed solution will be prevented. In practice, the appearance of the cooling sheet 161 can be irregular shape, radial structure or fin structure to increase the heat dissipation surface area of the cooling sheet 161.

In practice, the cooling device 16 may have a cooling pathway 163 formed in the gas generator. The external air flows through the cooling sheet 161 to take heat away from the cooling sheet 161 via the cooling pathway 163. The cooling pathway 163 has a flow inlet and a flow outlet. The flow inlet is configured for introducing the external air into the gas generator 1 to flow to the cooling sheet 161. The flow outlet is configured for outputting the air with the heat of the cooling sheet 161 to the outside of the gas generator. In an embodiment, the cooling pathway 163 does not contact the cooling sheet 161 directly but only introduces and outputs the air respectively. That is, the cooling pathway 163 only restricts the pathway of external air flowing into the gas generator 1 and the pathway of external air flowing out of the gas generator 1, but the cooling pathway 163 does not restrict the flowing way of the external air in the gas generator 1. Therefore, the external air is free to diffuse in the gas generator 1. In another embodiment, the flow inlet and the flow outlet are connected and the cooling pathway 163 contacts the cooling sheet 161 directly. The external air located in the cooling pathway 163 may take the heat away from the cooling sheet 161.

In an embodiment, the cooling device 16 further comprises a cooling pathway component 164 coupled to the cooling sheet 161. While the cooling pathway component 164 is combined with the cooling sheet 161, the cooling pathway 163 is formed. In an embodiment, a cooling fan 162 is configured at the flow inlet or the flow outlet to decrease the diameter limitation of the cooling pathway 163 and improve the convenience of installation. Besides, the cooling fan 162 can adjust the wind speed and the rotation direction of fan blade according to the preset temperature, wind speed or the detected environment temperature. The cooling fan 162 can further be a frequency conversion fan to save energy and improve cooling efficiency. In practice, the cooling fan 162 can be a axial flow fan to drive the external air to flow into the cooling pathway 163. In another embodiment, the cooling fan 162 can be a blast fan to decrease the thickness requirement of the cooling pathway 163. Furthermore, the cooling fan 162 can be configured more than one, and the plurality of cooling fans 162 are distributed in the cooling pathway 163 to increase the gas capacity flowing into the cooling pathway 163.

Since the cooling sheet 161 is cooled down by the external air, the larger the area of the external air flowing through the cooling sheet 161, the higher the cooling efficiency of the cooling sheet 161. In an embodiment, the cooling pathway 163 can lead the external gas to flow through most of the cooling sheet 161, so that the cooling efficiency is increased. Furthermore, the cooling pathway 163 is distributed the entire cooling sheet 161 to increase the cooling efficiency of the cooling sheet 161. In another embodiment, the entire cooling sheet 161 is contributed to formation of the cooling pathway 163, so that the external air may flow through the one side or entire cooling sheet 161.

Please refer to FIG. 1 again. In an embodiment, the gas generator 1 further comprises a gas filter device 18 coupled to the condensing filter device 14 for receiving and filtering the hydrogen filtered by the condensing filter device 14. Since the condensing filter device 14 is configured for cooling down the gas with high temperature and humidity, the filter material able to be used is limit. The hydrogen cooled down by the condensing filter device 14 is at lower temperature and humidity, so the different filter material can be configured for filtering the impurities again. The impurities may contain the electrolyte, metal impurities in the electrolytic water, organic impurities and other impure substances. The impurities may also be the unnecessary gas generated by electrolyzing the impure substances such as chlorine.

Figure 5:
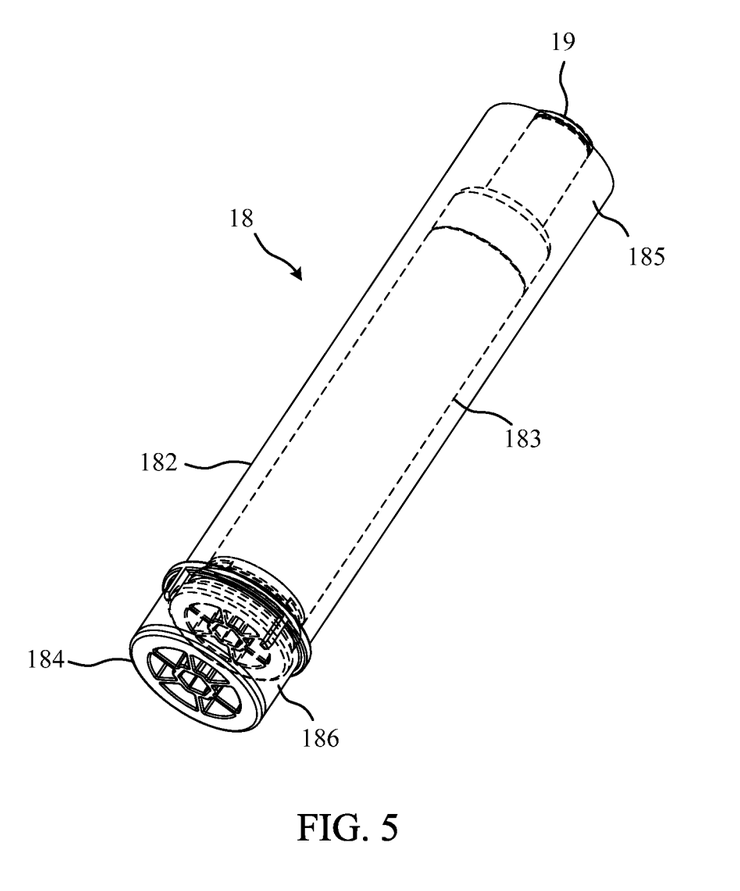
FIG. 5 shows a schematic diagram of an embodiment of the gas filter device of the gas generator of the present invention.

Please refer to FIG. 1 and FIG. 5. FIG. 5 shows a schematic diagram of an embodiment of the gas filter device 18 of the gas generator 1 of the present invention. Wherein, the gas filter device 18 has an outer wall 182 and an inner wall 183. The inner wall 183 is filled with an activated carbon 181 as a filter of the gas filter device 18 for filtering the impurities of the hydrogen received by the gas filter device 18. The hydrogen received by the gas filter device 18 flows into the inner wall 183 via the interspace between the outer wall 182 and the inner wall 183, and then the filtered hydrogen is exhausted outside the gas filter device 18. Wherein, the gas filter device 18 may be divided into a top 185 and a corresponding bottom 186. The hydrogen received by the gas filter device 18 flows into the interspace between the outer wall 182 and the inner wall 183 via the top 185. Then the hydrogen flows into the inner wall 183 filled with the activated carbon 181 via the bottom 186. And then the filter hydrogen is exhausted outside the gas filter device 18 via the top 185 again. Since the gas filter device 18 is configured for filtering the impurities of the gas, the filter in the gas filter device 18 should be cleaned or replaced regularly to maintain filtration efficiency. The gas filter device 18 may comprise a removable cover 184 to replace or wash the filter conveniently. In practice, the activated carbon 181 is accommodated in a space formed by the inner wall 183 and the cover 184.

Besides, the gas generator 1 further comprises a check valve 19 coupled to the gas filter device 18 for preventing the reverse flow in the gas generator 1. The check valve 19 can be configured at the inlet or the outlet of the gas filter device 18. Otherwise, the check valve 19 can be configured at a place before the gas flowing into or outside the gas filter device 18. Furthermore, the check valve 19 can be a flameproof device. In practice, in the event of an accident or system instability, the flames of the explosion or burning will spread via the tube to the source of the gas. The flameproof device is configured for preventing the reverse gas from introducing the flame to the source of the gas. Since the hydrogen generated by the electrolytic device 12 is at low humidity and high purity after cooling and filtering, the hydrogen is easier to ignite or explode. The check valve 19 is configured in the gas pathway to improve the using safety because the check valve 19 prevents the reverse gas to avoid the flames damaging the gas generator 1 component. Furthermore, the gas filter device 18 and the check valve 19 can be withdrawn from the gas generator 1 simultaneously to replace the filter.

Figure 4:
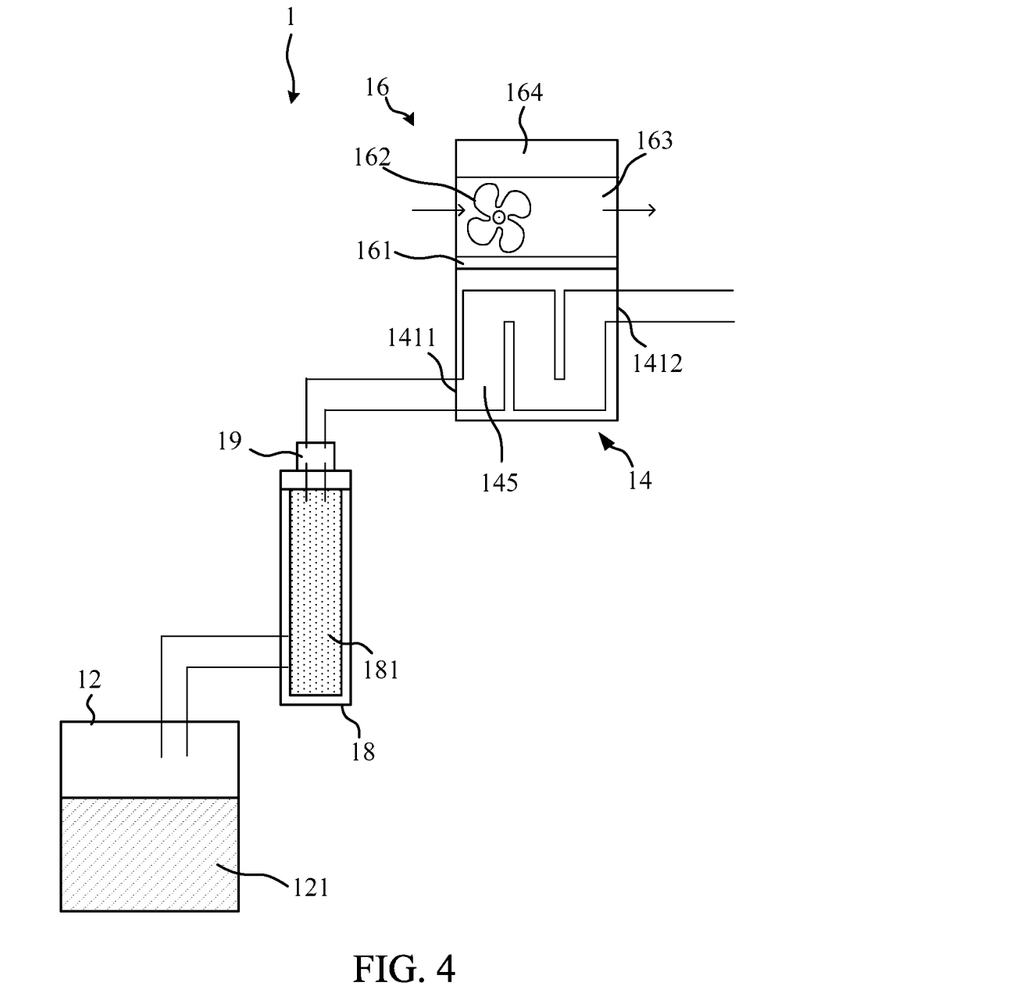
FIG. 4 shows a schematic diagram of another embodiment of the gas generator of the present invention.

Please refer to FIG. 4. FIG. 4 shows a schematic diagram of another embodiment of the gas generator of the present invention. The difference between the FIG. 1 and FIG. 4 is the gas filter device 18 coupled between the electrolytic device 12 and the condensing filter device 14, so that the gas generator 1 with a different connection form is generated. In practice, the gas generator 1 may further comprise a wetting device coupled to the electrolytic device 12 or the condensing filter device 14. The wetting device is configured for importing the high temperature gas generated by the electrolytic device 12 into a wetting liquid of the wetting device to decrease the temperature. Moreover, the impurities of the gas can be filtered by importing into the wetting liquid. The wetting liquid may be heated or volatilized by the high temperature gas to generate a volatile gas. The volatile gas is combined with the imported gas and outputted to the next device.

In practice, the gas generator 1 further comprises an atomizing device coupled to the condensing filter device 14 or the gas filter device 18. The atomizing device is configured for mixing the filtered hydrogen with atomized gas to form a healthy gas for further using. Wherein, the atomized gas is selected from one of the groups consisting of water vapor, atomized solution, volatile essential oil and combinations thereof. Besides, the atomizing device can be imported with atomized gas to combine with a filtered gas to form healthy gas; otherwise, the precursor of the atomized gas, such as essential oils, syrups, pure water, or the combinations thereof, can be shacked and atomized to form the atomized gas, and then the atomized gas combines with a filtered gas to form a healthy gas. The cooling device 16 may have an accommodating room for accommodating part of the atomizing device to reduce the volume of the gas generator 1. Therefore, the interspace can be utilized sufficiently, and the required volume can be reduced.

Please refer to FIG. 1, FIG. 2, and FIG. 3 again. Another aspect of the present invention is to provide a gas generator 1. According to an embodiment of the present invention, the gas generator 1 of the present invention comprises an electrolytic device 12, a condensing filter device 14, and a cooling device 16. The electrolytic device 12 accommodates electrolyzed water 121 and the electrolytic device 12 is configured for electrolyzing the electrolyzed water 121 to generate hydrogen. The condensing filter device 14 is coupled to the electrolytic device 12, and is configured for receiving the filter hydrogen. The cooling device 16 has a cooling pathway 163 and a plurality of flow openings 1631. The flow openings 1631 are located at the cooling pathway 163 respectively. The cooling device 16 further comprises a cooling sheet 161, a cooling pathway component 164, and a cooling fan 162. The cooling sheet 161 is coupled to the condensing filter device 14, and the cooling pathway component 164 is coupled to the cooling sheet 161. The cooling pathway 163 is formed between the cooling pathway component 164 and the cooling sheet 161, and the cooling fan 162 drives the external air to flow through the cooling pathway 163 via the openings 1631. Therefore, the temperature of the cooling sheet 161 is decreased, and then the temperature of the condensing filter device 14 is decreased along.

Wherein, the using elements and the connecting forms of the present embodiment can be applied to the embodiments described above. That is, the functions and patterns of the corresponding elements in the present embodiment are the same as the described embodiments in general, and it's unnecessary to go into details again.

Besides, the openings 1631 can be located at different sides of the cooling pathway 163 in practice, for example, the bottom side is away from the cooling sheet 161, and the front side and the rear side are at the same direction as the external air flowing. So that the external air in different positions can be sucked in, or the heating gas in different positions can be exhausted. Therefore, the heat accumulation around the cooling device 16 can be avoided.

In summary, the object of the present invention is to provide a gas generator comprising the electrolytic device, the condensing filter device, and the cooling device. In the gas generator of the present invention, the electrolytic device generates hydrogen for inhaling. The generated gas and the components are cooled down and filtered by the cooling device and the condensing filter device. Therefore, the gas generator works at stable operating temperature, and the gas generator elements are prevented from the damage by the high temperature and the high humidity gas damage. Therefore, the operational safety is improving and the life of the gas generator is extending.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A gas generator, comprising:
   an electrolytic device accommodating an electrolyzed water; wherein the electrolytic device is configured for electrolyzing the electrolyzed water to generate hydrogen;
   a condensing filter device further comprising a gas pathway, a filter material, and a spacer; wherein the gas pathway is horizontally arranged and comprises a condensing inlet and a condensing outlet, the condensing inlet is configured for receiving the hydrogen, and the filter material is configured within the gas pathway to filter the hydrogen, and the spacer is configured within the condensing filter device for limiting the movement of the filter material within the gas pathway, the condensing outlet is configured for outputting the filtered hydrogen; and
   a cooling device comprising a cooling sheet; wherein the cooling sheet is coupled to the condensing filter device for conducting heat of the condensing filter device.

2. The gas generator of claim 1, further comprising an atomizing device coupled to the condensing filter device; wherein, the atomizing device is configured for receiving the filtered hydrogen, and the atomizing device generates atomized gas to be mixed with the filtered hydrogen, and the cooling device has an accommodating space for accommodating part of the atomizing device.

3. The gas generator of claim 1, wherein the cooling device has a cooling pathway formed within the cooling device, and the cooling device is configured to drive air to flows through the cooling pathway.

4. The gas generator of claim 3, wherein the cooling device comprises a cooling pathway component coupled to the cooling sheet, and the cooling pathway is formed between the cooling pathway component and the cooling sheet.

5. The gas generator of claim 3, wherein the cooling device further comprises a cooling fan to drive the air to flow into the cooling pathway, and the cooling fan is a blast fan accommodated within the cooling pathway.

6. The gas generator of claim 1, further comprising a gas filter device coupled to the condensing filter device, wherein the gas filter device is configured for further filtering the hydrogen.

7. The gas generator of claim 6, further comprising a check valve coupled to the gas filter device.

8. The gas generator of claim 7, wherein the gas filter device has an outer wall and an inner wall, and inside the inner wall is filled with activated carbon, and the outer wall is located outside the inner wall, and the hydrogen received by the gas filter device flows into the inner wall via the interspace between the outer wall and the inner wall, and then the hydrogen is exhausted outside the gas filter device.

9. The gas generator of claim 8, wherein the gas filter device comprises a removable cover, and the activated carbon is accommodated within a space formed by the inner wall and the cover, and the gas filter device and the check valve can be simultaneously withdrawn from the gas generator.

10. The gas generator of claim 1, wherein the filter material is composed of a plurality of filter pieces, and the spacer prevents the filter pieces from connecting to each other directly.

11. A gas generator, comprising:
    an electrolytic device accommodating an electrolyzed water; wherein the electrolytic device is configured for electrolyzing the electrolyzed water to generate hydrogen;
    a condensing filter device coupled to the electrolytic device, the condensing filter device comprising a horizontal gas pathway configured for receiving and filtering the hydrogen; and a cooling device, having a cooling sheet coupled to the condensing filter device for conducting heat of the condensing filter device; and an atomizing device coupled to the condensing filter device, wherein the atomizing device is configured to receive the filtered hydrogen and generate atomized gas to be mixed with the filtered hydrogen.

12. The gas generator of claim 11, further comprising an atomizing device coupled to the condensing filter device, wherein the atomizing device is configured for receiving the filtered hydrogen, and the atomizing device generates atomized gas to be mixed with the filtered hydrogen, and wherein the cooling device has a cooling pathway component coupled to the cooling sheet to form a cooling pathway between the cooling pathway component and the cooling sheet, and the cooling device has an accommodating space for accommodating part of the atomizing device.

13. The gas generator of claim 12, wherein the cooling device further comprises a cooling fan to drive air to flow into the cooling pathway, the cooling fan is a blast fan accommodated within the cooling pathway.

14. The gas generator of claim 11, further comprising a gas filter device coupled to the condensing filter device, wherein the gas filter device is configured for further filtering the hydrogen.

15. The gas generator of claim 14, further comprising a check valve coupled to the gas filter device.

16. The gas generator of claim 15, wherein the check valve is a flameproof device.

17. The gas generator of claim 15, wherein the check valve receives the hydrogen exhausted by the gas filter device.

18. The gas generator of claim 15, wherein the gas filter device has an outer wall and an inner wall, and inside the inner wall is filled with activated carbon, and the outer wall is located outside the inner wall, and the hydrogen received by the gas filter device flows into the inner wall via the interspace between the outer wall and the inner wall, and then the hydrogen is exhausted outside the gas filter device.

19. The gas generator of claim 18, wherein the gas filter device comprises a removable cover, and the activated carbon is accommodated within a space formed by the inner wall and the cover, and the gas filter device and the check valve can be simultaneously withdrawn from the gas generator.

20. The gas generator of claim 18, wherein the gas filter device has a top and a bottom, and the hydrogen received by the gas filter device flows into the interspace between the outer wall and the inner wall via the top, and then the hydrogen flows into the inner wall via the bottom and is exhausted outside the gas filter device via the top.

* * * * *